(12) United States Patent
Schilling et al.

(10) Patent No.: US 7,972,613 B2
(45) Date of Patent: Jul. 5, 2011

(54) INSECT SCREENING SHEET

(75) Inventors: Andreas Schilling, Hagendorn (CH); Stanislav N. Horb, Leonberg (DE)

(73) Assignees: OVD Kinegram AG, Zug (CH); Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 179 days.

(21) Appl. No.: 12/227,475

(22) PCT Filed: Jun. 1, 2007

(86) PCT No.: PCT/EP2007/004871
§ 371 (c)(1),
(2), (4) Date: Jan. 29, 2009

(87) PCT Pub. No.: WO2007/140937
PCT Pub. Date: Dec. 13, 2007

(65) Prior Publication Data
US 2009/0232862 A1   Sep. 17, 2009

(30) Foreign Application Priority Data
Jun. 3, 2006  (DE) .......................... 10 2006 026 099

(51) Int. Cl.
*A01N 25/34* (2006.01)
(52) U.S. Cl. ........................... 424/409; 424/405; 43/119
(58) Field of Classification Search .................. 424/405, 424/409
See application file for complete search history.

(56) References Cited

U.S. PATENT DOCUMENTS

| 5,303,502 | A | 4/1994 | Metzner et al. |
| 6,027,740 | A | 2/2000 | Puterka et al. |
| 2004/0184151 | A1* | 9/2004 | Schilling et al. ............... 359/529 |
| 2010/0119780 | A1* | 5/2010 | Schilling et al. ............... 428/172 |
| 2010/0173133 | A1* | 7/2010 | Tompkin et al. ............... 428/172 |

FOREIGN PATENT DOCUMENTS

WO    WO 92/19101    11/1992

* cited by examiner

*Primary Examiner* — Neil Levy
(74) *Attorney, Agent, or Firm* — Hoffman & Baron, LLP

(57) ABSTRACT

Described is an insect screening sheet having an insect-repellent layer (10) in which the insect-repellent layer (10) has a three-dimensional surface structure which comprises a regularly periodically and/or statistically distributed coarse structure (12g) and/or nanostructure (12n).

24 Claims, 3 Drawing Sheets

INSECT SCREENING SHEET

This application claims priority based on an International Application filed under the Patent Cooperation Treaty, PCT/EP2007/004871, filed on Jun. 1, 2007 and German Application No. DE 102006026099.6-23, filed on Jun. 3, 2006.

BACKGROUND OF THE INVENTION

The invention concerns an insect screening sheet having an insect-repellent layer.

Numerous devices and methods are known for providing protection from insects.

To protect fruit trees and the like from creeping insects or insect larvae, for example sheets with a sticky surface are known, on which the insects or insect larvae remain stuck. It will be noted however that sticky surfaces can lose something of their effect due to contamination and/or due to the adhesive being washed off.

Protective paints are also known, which however can entail unwanted environmental pollution, particularly if they involve toxic paints.

SUMMARY OF THE INVENTION

The object of the invention is now that of providing an inexpensive device which is easy to handle and which permits durable and environmentally friendly protection from insects.

The object of the invention is attained by an insect screening sheet having an insect-repellent layer, wherein it is provided that the insect-repellent layer has a three-dimensional surface structure with statistically and/or periodically distributed coarse structure elements and/or statistically and/or periodically distributed fine structure elements.

It can also be provided in that respect that there are structure sizes on more than two size scales (coarse/fine) or there can be a continuous distribution of structure sizes over a relatively great range.

The proposed insect screening sheet is distinguished in that it prevents or greatly reduces the adhesion between the insect and the insect screening sheet by means of the special surface structure of the insect-repellent layer. That surface structure is such that the insects or the insect larvae which are to be repelled cannot adhere thereto and thus cannot pass the regions provided with the insect screening sheet. That effect is based on the fact that the suction pads of the insects or the insect larvae are unable to adapt to the constantly changing nature of the surface structure according to the invention. The continual change between coarse and fine structure elements means that no adhesion strategy is afforded so that the insect or the insect larva slips off the surface of the insect screening sheet. The insect-repellent effect is enhanced if the insect screening sheet is arranged perpendicularly or at a steep angle.

Because the insect-repellent effect is based exclusively on the nature according to the invention of the surface structure of the insect-repellent layer which does not give off any substances into the environment, the environment enjoys optimum protection. The sheet according to the invention further avoids exterminating the insects including the useful or beneficial insects, as is the case when using adhesive strips or insecticides, or adversely affecting insect-eating animals due to contaminated insects.

The surface structure of the insect-repellent layer can be shaped with the known shaping methods for sheet production in a roll-to-roll process, for example by hot embossing of a thermoplastic replication lacquer or by cold embossing and hardening of a UV-hardenable replication lacquer.

Further advantageous configurations are set forth in the appendant claims.

It can be provided that the dimensions of the structure elements such as width, height and lateral spacing, are $\leq 100$ µm.

It can further be provided that the dimensions of the fine structure elements such as width, height and lateral spacing are in the range of between 5 nm and 1,000 nm, preferably between 5 nm and 200 nm.

The dimensions of the coarse structure elements such as width, height and lateral spacing can be in the range of between 2 µm and 100 µm.

It can be provided that the coarse structure has between 5 and 1,000 times greater typical structure parameters such as width, depth and lateral spacing of the structure elements than the fine structure.

It can be provided that the average number of structure elements per millimeter is between 10 and $5 \cdot 10^5$.

It can further be provided that the fine structure has an average depth of between 5 nm and 1,000 nm, preferably between 5 nm and 200 nm, with a maximum depth of between 10 nm and 1,000 nm, preferably between 10 nm and 300 nm.

An advantageous configuration provides that the fine structure has an average depth-to-width ratio of between 0.3 and 5. The dimension-less depth-to-width ratio, also referred to as the aspect ratio, relates the depth of the "trough" between two adjacent raised portions to the spacing of the "peaks" of two adjacent raised portions.

The fine structure can therefore be characterized by parameters such as the average depth, the maximum depth and a typical average depth-to-width ratio, as described hereinbefore.

It can further be provided that the fine structure is a stochastic fine structure. Although the depth-to-width ratio of a stochastic fine structure is the average value of all local depth-to-width ratios, the depth-to-width ratio is thus nonetheless also an important feature of the stochastic fine structure. The depth-to-width ratio determines for example the size of the upper contact face of the fine structure which, with suitable dimensioning, can be so small that it is for example no longer possible for an insect leg to adhere to that contact face.

An advantageous configuration provides that the stochastic fine structure is a matt structure. Due to that additional optical property the insect-repellent layer appears less conspicuous for no light reflections are produced, which can be unwanted for example in public installations and situations.

It can also be provided that the fine structure is a non-stochastic fine structure, for example a regular grating structure or a combination of a stochastic and a non-stochastic structure.

An advantageous configuration provides that the coarse structure is a regular grating structure. In that respect it is further also possible for the grid raster widths of the grating structure to differ in the x and y direction or for the grating structure to be a geometrically transformed grating structure, for example with corrugations or circular co-ordinate axes in the x and/or y direction.

It can further be provided that the regular grating structure is in the form of a function of the co-ordinates x and/or y, which periodically varies the depth of the grating structure in the x direction and/or in the y direction. This can involve for example a quadratic sine function which provides rib-shaped or knob-shaped raised portions, wherein production of a master for shaping the grating structure requires comparatively little complication and expenditure.

It can be provided that the spacing between two adjacent raised portions of the grating structure is between 0.3 μm and 10 μm.

It can further be provided that the grating structure has a depth-to-width ratio of >1.

A further advantageous configuration provides that the three-dimensional surface structure has first regions with a coarse structure in the form of a periodic structure and second regions with a fine structure in the form of a periodic structure, wherein it is provided that the first and second regions are mingled with each other.

In regard to the combination or mingling of the fine structures and the coarse structures it can be provided that the fine structures are afforded in regions of the coarse structure, for example on the bottom of the "troughs" of the coarse structure. It can however also be provided that the fine structures are superimposed on the coarse structure, that is to say modulate the contours of the coarse structure. In that respect it can further be provided that modulation is effected only in region-wise manner, for example only the "peak regions" and/or the "troughs" of the coarse structure are modulated with the fine structure. Advantageously however it can also be provided that the structure elements of the coarse structure and the fine structure are mingled with each other, in which respect random distribution offers further advantages.

In addition there can be provided surface structures in which the dimensions of the structure elements are between 5 nm and 100 μm and in which the structure elements are of such a configuration that the coarse structure blends fluidly into fine structure. The typical dimensions of the structure element extend in that respect approximately over two orders of magnitude.

Advantageously the structure elements can also differ from each other in respect of their form. That can provide a practically unlimited number of different structure elements which afford a particularly good insect protection effect if they are distributed densely in a random arrangement on the surface of the insect screening sheet and in that way provide the insect-repellent surface structure. Such a surface structure can be advantageously described by specifying the average values of all structure parameters as well as the limit values of all structure parameters.

It can be provided that the insect-repellent layer is in the form of a layer of a transfer layer assembly of a transfer film.

It can also be provided that the insect-repellent layer is in the form of a layer of a lamination film. In that case the insect-repellent layer can be arranged on a carrier layer of a thickness of between 12 and 100 μm. The carrier layer can be for example in the form of a carrier film of PVC or PET.

It can further be provided that the insect-repellent layer is of a thickness of between 0.3 μm and 50 μm. The dimensioning of the thickness of the insect-repellent layer can be adapted for example to the desired tearing strength of the layer and/or the maximum roughness depth of the surface structure. The roughness depth of the insect sheet is a parameter which is adapted to the measurement technology and which involves the above-indicated depths of the coarse structure and the fine structure as well as the arrangement in respect of height of the structure elements. The structure elements can have for example a common lower reference plane and can thus be arranged in flush relationship in respect of the base thereof. The structure elements can further have a common upper reference plane and can thus be arranged in flush relationship in respect of the top thereof, or they can assume any positions between the two extreme positions.

It can be provided for example that the thickness of the insect-repellent layer is between 2 and 3 times the maximum roughness depth of the surface structure thereof.

Further advantageous configurations relate to layers of the insect screening sheet which are arranged on or under the insect-repellent layer. In that respect the top side of the insect-repellent layer is the side which is formed with the insect-repellent surface structure.

It can be provided that the rear side of the insect screening sheet is covered with an adhesive layer. The adhesive layer can be a cold adhesive which is optionally covered by a protection layer which is withdrawn prior to application of the insect screening sheet.

It can be provided that the insect-repellent layer is covered with at least one water-soluble and/or biologically decomposable protection layer. That protection layer can further also be in the form of a release layer which additionally prevents an adhesive layer arranged at the underside of the insect screening sheet from adhering to the top side of the insect-repellent layer and thus permits the insect screening sheet to be rolled up. In that way it is also possible to dispense with the provision of a protection layer which can be pulled off the insect screening sheet, when using a cold adhesive.

A further configuration provides that the rear side of the insect screening sheet is provided with a touch-and-close fastener. The touch-and-close fastener can be provided for fixing on rough surfaces or on a further touch-and-close fastener, in which respect easy releasability of the touch-and-close fastener facilitates release of the insect screening sheet when not in use.

It can further be provided that the insect screening sheet is of a transparent configuration. A transparent insect screening sheet is optically inconspicuous, particularly if it has a low reflection capability, as described hereinbefore.

It can also be provided that the insect screening sheet is opaque. An advantageous configuration provides that the insect screening sheet is colored white, by for example the provision of a white lacquer layer underneath the insect-repellent layer or by a white pigment being added to the insect-repellent layer. In particular white annular protection layers have proven their worth for fruit trees in order to prevent tearing of the bark on sunny frosty days. It is therefore possible to provide that the insect screening sheet can also be used as frost protection, besides affording protection from insects.

The insect screening sheet according to the invention can be manufactured in many different ways.

It can be provided that the insect screening sheet is in the form of a transfer film having a carrier film and a transfer layer assembly which can be released from the carrier film and the insect-repellent layer is arranged in the transfer layer assembly as a layer of the transfer layer assembly.

It is possible to provide an insect-repellent adhesive strip which for example is wound up to afford an adhesive strip roll, wherein the top side of the insect-repellent layer of the adhesive strip, the top side possibly being provided with a protection layer, faces outwardly, and thus at the same time protects the adhesive layer of the adhesive strip from contamination or the like.

It can additionally be provided that a release layer is arranged on the top side of the insect-repellent layer or the insect-repellent layer is in the form of a release layer which permits release of the adhesive layer from the insect-repellent layer and thus permits the adhesive strip to be rolled up.

In addition there can be provided an insect-repellent strip or an insect-repellent film provided preferably region-wise with a touch-and-close fastener. A film of large area can be used for the protection of film beds. The insect-repellent layer of the sheet can be applied to a carrier film, for example to a PVC film of a thickness of between and 12 and 35 μm, to increase the tearing strength. This however may also be a particularly thin film which clings by adhesion to surfaces of any shape, for example to the outside of the window panes of a greenhouse.

The insect screening sheet can have its own fixing means such as an adhesive layer or a touch-and-close fastener layer, but it can also be provided that the insect screening sheet is fixed with external means, for example with an adhesive strip or with staples or the like or it is clamped in position, for example between a window frame and a window.

In addition the insect screening sheet can be provided with a water-soluble and/or biologically decomposable protection layer, as described hereinbefore. Such a protection layer can be washed off for example by natural precipitation and thus activated. That can provide for example that firstly useful or beneficial insects can unimpededly pass the insect screening sheet but harmful insects which arrive later cannot pass the insect-repellent surface, which is now activated, of the insect screening sheet.

In addition there is provided an insect-repellent suspension having particles in flake form of the insect-repellent layer. After evaporation of the liquid in which the particles in flake form are distributed, the particles in flake form constitute a continuous insect-repellent particle layer. It can advantageously be provided that the particles in flake form have the insect-repellent surface structure on both sides so that the insect-repellent action occurs independently of the position of use of the particles in flake form. The liquid in the above-mentioned suspension can advantageously be a lacquer, the binding agent of which imparts the permanent adhesion for the particles in flake form on the substrate provided with the suspension.

BRIEF DESCRIPTION OF THE DRAWINGS

The invention is described by way of example hereinafter by means of a number of embodiments with reference to the accompanying drawings in which.

DETAILED DESCRIPTION OF THE INVENTION

Figure 1:
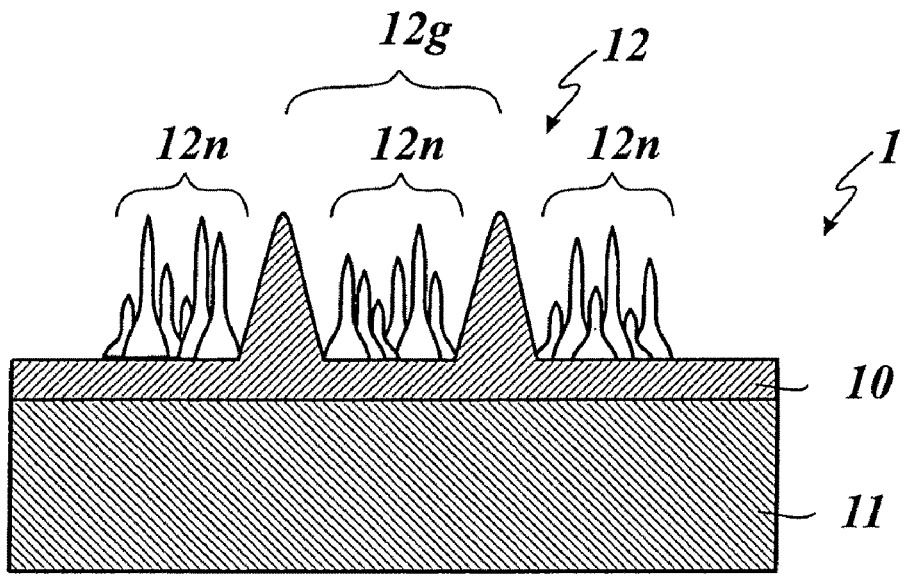
FIG. 1 shows a diagrammatic view in section of a first embodiment of the insect screening sheet according to the invention.

FIG. 1 shows an insect protection or screening sheet 1 having an insect-repellent layer 10 with a surface profile 12 and a carrier layer 11. The carrier layer 11 is formed from a PVC film of a thickness of between 12 and 35 μm. The insect-repellent layer 10 can be formed for example from a thermoplastic material or from a UV-hardenable lacquer of a thickness of between 1 and 30 μm. In addition it is also possible to provide between the carrier layer 11 and the insect-repellent layer 10 one or more further layers for example bonding agent layers, decorative layers or also metallic layers.

The surface profile 12 of the insect-repellent layer 10 is formed from a regular grating structure 12g and stochastic fine structures 12n which, because of their structure parameters which are in the nanometer range, are referred to hereinafter as nanostructures. The nanostructures 12n are arranged in the "troughs" of the grating structure 12g. The grating structure 12g is a two-dimensional grating structure having mutually spaced conical raised portions arranged in a square raster grid.

The nanostructures 12n are formed from randomly distributed raised portions which are of a random height and a random configuration, wherein the base faces of the raised portions are arranged in a common plane. It can however also be provided that the tips of the raised portions lie in a common plane or that neither the base faces nor the tips of the raised portions lie in a common plane.

The function-determining parameters such as the mean spacing between two raised portions or the depth of the "troughs" in which the nanostructure 12n and the grating structure 12g are provided differ approximately by a factor of 10. The nanostructure 12n has function-determining parameters in the nanometer range, and the grating structure 12g has function-determining parameters in the micrometer range. The grating structure 12g is therefore a coarse structure in comparison with the nanostructure 12n.

The protection action in relation to insects arises out of the fact that the surface of the insect-repellent layer, by virtue of the above-described configuration, prevents the insects from clinging thereto because it is formed with a locally changing surface profile to which the insect or insect larva foot is unable to adapt. Creeping or running insects or other small living beings can therefore not pass over the region covered by the insect screening sheet, particularly if that region is arranged perpendicularly.

Figure 2:
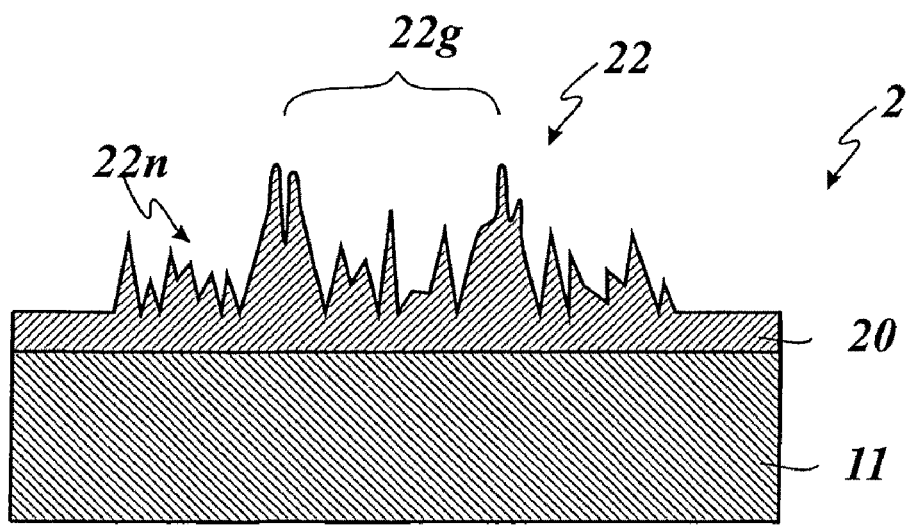
FIG. 2 shows a diagrammatic view in section of a second embodiment of the insect screening sheet according to the invention.

FIG. 2 now shows an insect screening sheet 2 which differs from the insect screening sheet 1 described with reference to FIG. 1, in regard to the configuration of the surface structure of the insect-repellent layer. The insect screening sheet 2 has an insect-repellent layer 20 with a surface profile 22 in which stochastic nanostructures 22n are superimposed on a regular grating structure 22g. The grating structure 22g is a one-dimensional grating structure having mutually spaced ribs of approximately triangular cross-section, which are arranged in a linear raster.

The nanostructures 22n are formed from randomly distributed raised portions and recesses respectively which project out of the surface of the grating structure 22g and/or project into the surface of the grating structure 22g. The raised portions or recesses are of a random height and a random configuration, in which respect for the sake of better illustration FIG. 2 shows only the raised portions and recesses which are in the section plane. The raised portions or recesses of the nanostructures 22n are therefore not rib-shaped raised portions or groove-shaped recesses, but raised portions and recesses which are distributed randomly over the entire surface of the grating structure 22g and which are formed randomly and which are approximately conical.

Figure 3:
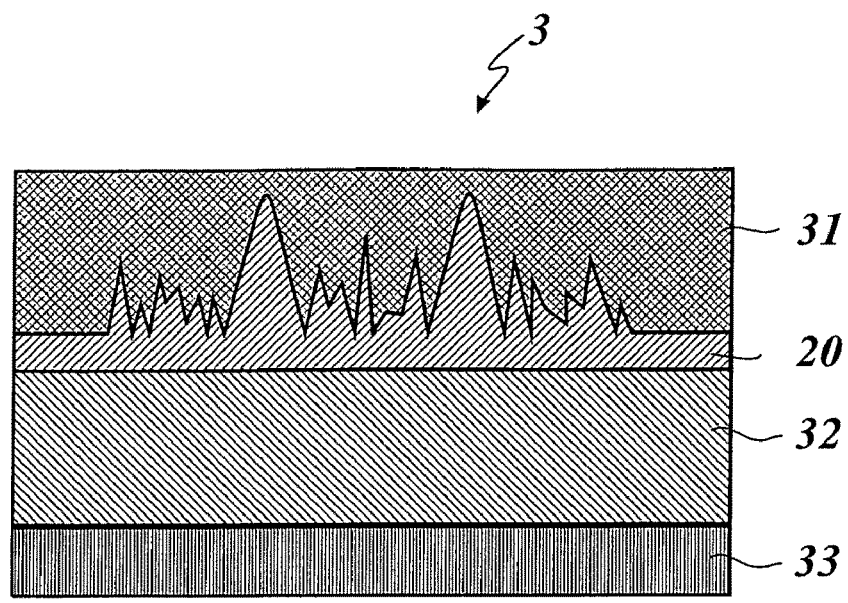
FIG. 3 shows a diagrammatic view in section of a third embodiment of the insect screening sheet according to the invention.

FIG. 3 now shows an adhesive strip 3 including an adhesive layer 33, a carrier layer 32, the above-described insect-repellent layer 20 (see FIG. 2) and a protection layer 31. The protection layer 31 covers the function-determining surface structure (see FIG. 2) of the insect-repellent layer 20 and protects it from damage and/or contamination until it is used. The protection layer 31 is preferably a water-soluble protection layer which can be washed off for example by the action of rain.

The underside of the insect-repellent layer 20 is connected to the carrier layer 32 which in the illustrated embodiment is in the form of a PVC film of a thickness of between 12 and 35 μm. The carrier layer 32 imparts sufficient strength to the adhesive strip 3, to fix it for example in the form of a protective ring to the trunk of a fruit tree. The underside of the carrier layer 32 is provided with the adhesive layer 33. In the illustrated embodiment the adhesive layer 33 is not covered by a further protection layer because it is provided that the adhesive strip 3 is marketed wound up to form a roll, in which case the top side of the protection layer 31 faces outwardly and therefore in the rolled-up condition of the adhesive strip 3 at the same time forms a protection layer for the adhesive layer 33. The adhesive layer 33 can be a cold adhesive, as is usually employed for adhesive strips.

Figure 4:
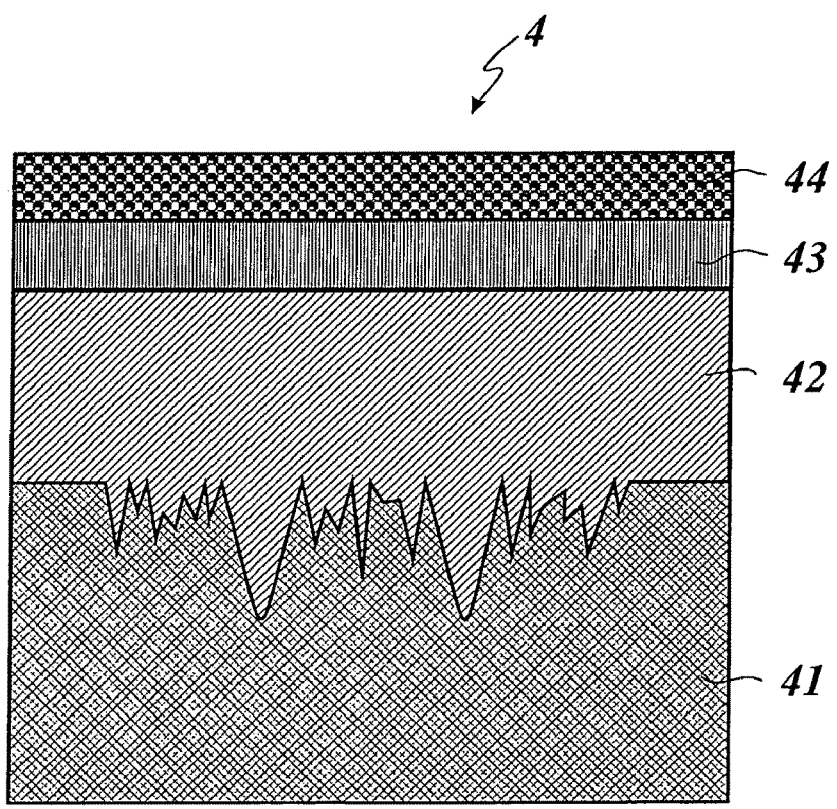
FIG. 4 shows a diagrammatic view in section of a fourth embodiment of the insect screening sheet according to the invention.

FIG. 4 shows a transfer film 4 with a carrier film 41 which at the same time is in the form of a replication layer. The carrier film 41 can be between 21 and 35 μm in thickness and can be made from a thermoplastic material such as PE. A master profile is shaped into the surface of the carrier film 41 by means of hot embossing, the master profile determining the surface structure of an insect-repellent layer 42 applied to the carrier film 41. It is possible to provide between the carrier film 41 and the insect-repellent layer 42 a separation layer or a release layer which facilitates later release of the insect-repellent layer 42 from the carrier film 41. The insect-repellent layer 42 is between 12 and 35 μm in thickness. Applied to the side of the insect-repellent layer 42, that is remote from the carrier film 41, is an adhesive layer 43 covered by a protection layer 44. The protection layer 44 can be pulled off the adhesive layer 43 prior to application of the transfer film 4, then the carrier film 41 can be pulled off the insect-repellent layer 42.

Figure 5A:
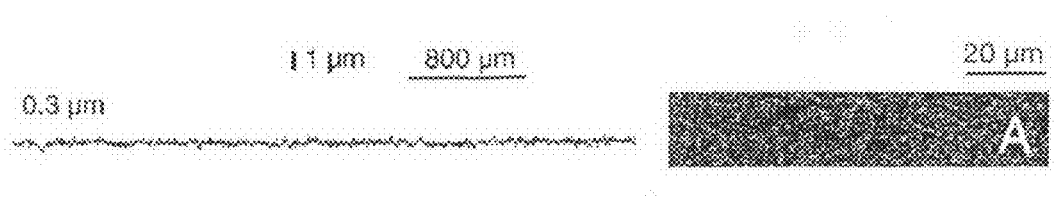
FIGS. 5a and 5b show a profile configuration and a plan view of a fifth embodiment of the insect screening sheet according to the invention.

FIGS. 5*a*, *b* and 6 now show typical profile forms of practical implementations of insect screening sheets. Both embodiments involve stochastic structures with configurations on different size scales with typical structure depths for the coarse structure of some micrometers.

Figure 5B:
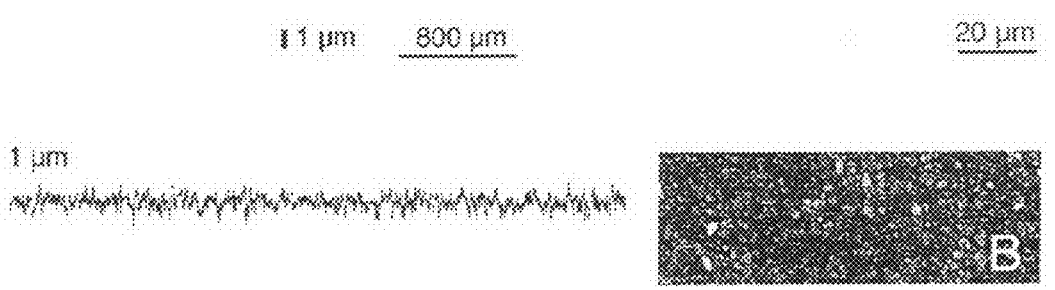

The insect screening sheets identified by (A) and (B) in FIGS. 5*a* and 5*b* were produced in the form of UV-replicated films and have proven to be highly successful in practical insect tests. In the tests the insect screening sheets were disposed perpendicularly or at a very steep angle.

The sheet shown in FIG. 5*a* has structure depths in the range of between 3 and 500 nm, while the sheet shown in FIG. 5*b* has structure depths in the range of between 1 and 2 μm.

Figure 6:
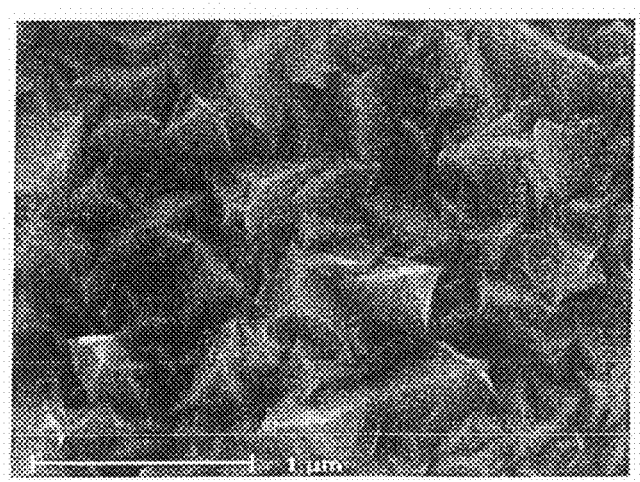
FIG. 6 shows a plan view of a sixth embodiment of the insect screening sheet according to the invention.

FIG. 6 shows by way of example a plan view on a further enlarged scale of an insect screening sheet, the structure elements of which involve widths of between 5 and 500 nm. In that respect it can be particularly clearly seen that the structure elements are randomly distributed and of random nature both in respect of their size and also their form. Insects are unable to cling to such a surface because they are unable to adapt to the continuously changing surface conditions.

The surface structures shown in FIGS. 5*a* through 6 can be produced for example by exposure of a photolacquer layer through a matt glass or the like and subsequent removal of the non-exposed regions and hardening of the photolacquer layer. It is also possible in that way to produce the master for a replication roller which can be used in a roll-to-roll process for the production of the insect screening sheet.

The invention claimed is:

1. An insect screening sheet having an insect-repellent layer, wherein the insect-repellent layer has a three-dimensional surface structure with statistically and/or periodically distributed coarse structure elements and statistically and/or periodically distributed fine structure elements and the surface structure is shaped in the insect-repellent layer by hot embossing or cold embossing,
   wherein the dimensions of the width, height and lateral spacing of the fine and coarse structure elements are <100 μm, and wherein the dimensions of the width, height and lateral spacing of the fine structure elements are in the range of between 5 nm and 1,000 nm, and wherein the dimensions of the width, height and lateral spacing of the coarse structure elements are in the range of between 2 μm and 100 μm.

2. An insect screening sheet as set forth in claim 1, wherein the coarse structure has between 5 and 1,000 times greater typical structure parameters such as width, depth and lateral spacing of the structure elements than the fine structure.

3. An insect screening sheet as set forth in claim 1, wherein the average number of structure elements per millimeter is between 10 and $5 \cdot 10^5$.

4. An insect screening sheet as set forth in claim 1, wherein the fine structure has an average depth of between 5 nm and 1,000 nm with a maximum depth of 1,000 nm.

5. An insect screening sheet as set forth in claim 1, wherein the fine structure has an average depth-to-width ratio of between 0.3 and 5.

6. An insect screening sheet as set forth in claim 1, wherein the fine structure is a stochastic fine structure.

7. An insect screening sheet as set forth in claim 6, wherein the stochastic fine structure is a matt structure.

8. An insect screening sheet as set forth in claim 1, wherein the fine structure is a non-stochastic fine structure.

9. An insect screening sheet as set forth in claim 1, wherein the coarse structure is a regular grating structure.

10. An insect screening sheet as set forth in claim 9, wherein the regular grating structure is in the form of a function of the coordinates x and/or y, which periodically varies the depth of the grating structure in the x direction and/or in the y direction.

11. An insect screening sheet as set forth in claim 9, wherein the spacing between two adjacent raised portions of the grating structure is between 0.3 μm and 10 μm.

12. An insect screening sheet as set forth in claim 9, wherein the grating structure has a depth-to-width ration of >1.

13. An insect screening sheet as set forth in claim 1, wherein the three-dimensional surface structure has first regions with a coarse structure in the form of a periodic structure and second regions with a fine structure in the form of a periodic structure, wherein it is provided that the first and second regions are mingled with each other.

14. An insect screening sheet as set forth in claim 1, wherein the insect screening sheet has a carrier film of a thickness of between 12 μm and 100 μm.

15. An insect screening sheet as set forth in claim 1, wherein the insect-repellent layer is of a thickness of between 0.3 μm and 50 μm.

16. An insect screening sheet as set forth in claim 1, wherein the insect-repellent layer is covered with at least one water-soluble and/or biologically decomposable protection layer.

17. An insect screening sheet as set forth in claim 1, wherein the rear side of the insect screening sheet is provided with an adhesive layer.

18. An insect screening sheet as set forth in claim 1, wherein the rear side of the insect screening sheet is provided with a touch-and-close fastener.

19. An insect screening sheet as set forth in claim 1, wherein the insect screening sheet is of a transparent configuration.

20. An insect screening sheet as set forth in claim 1, wherein the insect screening sheet is of an opaque configuration.

21. An insect screening sheet as set forth in claim 1, wherein the insect screening sheet is colored white.

22. An insect screening sheet as set forth in claim 1, wherein the insect screening sheet is in the form of a transfer film having a carrier film and a transfer layer assembly which can be released from the carrier film and the insect-repellent layer is arranged in the transfer layer assembly as a layer of the transfer layer assembly.

23. An insect screening sheet as set forth in claim 1, wherein the insect screening sheet is in the form of an adhesive strip which is wound to form a roll and which includes the insect-repellent layer and an adhesive layer arranged on the underside of the adhesive strip, and that a release layer is arranged on the top side of the insect-repellent layer or the insect-repellent layer is in the form of a release layer which permits the adhesive strip to be rolled up.

24. An insect-repellent suspension containing particles in flake form of the insect screening sheet as set forth in claim 1.

* * * * *

UNITED STATES PATENT AND TRADEMARK OFFICE
CERTIFICATE OF CORRECTION

PATENT NO. : 7,972,613 B2  Page 1 of 1
APPLICATION NO. : 12/227475
DATED : July 5, 2011
INVENTOR(S) : Schilling et al.

It is certified that error appears in the above-identified patent and that said Letters Patent is hereby corrected as shown below:

IN THE CLAIMS:

Column 9, line 10,
Claim 21            now reads "An insect screening sheet as set forth in claim 1,"
                    should read --An insect screening sheet as set forth in claim 20,--

Signed and Sealed this
Fourth Day of June, 2013

Teresa Stanek Rea
*Acting Director of the United States Patent and Trademark Office*